United States Patent
Khanzhin et al.

(10) Patent No.: US 7,683,058 B2
(45) Date of Patent: Mar. 23, 2010

(54) SUBSTITUTED PYRIMIDINE DERIVATIVES

(75) Inventors: Nikolay Khanzhin, Humlebæk (DK); Daniel Rodriguez Greve, Stenløse (DK); Mario Rottländer, Greve (DK)

(73) Assignee: H. Lundbeck A/S, Valby (DK)

(*) Notice: Subject to any disclaimer, the term of this patent is extended or adjusted under 35 U.S.C. 154(b) by 680 days.

(21) Appl. No.: 11/516,221

(22) Filed: Sep. 6, 2006

(65) Prior Publication Data
US 2007/0066612 A1    Mar. 22, 2007

Related U.S. Application Data

(60) Provisional application No. 60/715,988, filed on Sep. 9, 2005.

(30) Foreign Application Priority Data
Sep. 9, 2005    (DK) ............................... 2005 01262

(51) Int. Cl.
C07D 239/50    (2006.01)
A61K 34/505    (2006.01)

(52) U.S. Cl. .................... 514/235.8; 514/256; 544/122; 544/329

(58) Field of Classification Search ................. 544/122, 544/329; 514/235.8, 256
See application file for complete search history.

(56) References Cited

U.S. PATENT DOCUMENTS
2004/0009988 A1* 1/2004 Dodic .................. 514/252.14

FOREIGN PATENT DOCUMENTS
EP    1 334 972 A1    8/2003
WO    WO 02/066036 A1    8/2002
WO    WO 2006/064277 A1    6/2006

OTHER PUBLICATIONS

Von Bebenburg et al., CAPLUS Abstract 93:95058, 1980.*
Yi et al., Colloqium: Controlling potassium channel activities: Interplay between the membrane and intracellular factors, PNAS, vol. 98, No. 20, Sep. 25, 2001.*
Damasio, Alzheimer's Disease and Related Dementias, Cecil Textbook of Medicine, 20$^{th}$ Edition, vol. 2, pp. 1992-1996, 1996.*
Layzer, Degenerative diseases of the nervous system, Cecil Textbook of Medicine, 20$^{th}$ Edition, vol. 2, pp. 2050-2057, 1996.*
Wickenden, Alan D., et al., "Retigabine, A Novel Anti-Convulsant, Enhances Activation of KCNQ2/Q3 Potassium Channels", Molecular Pharmacology, Sep. 2000, pp. 591-600, vol. 58, No. 3, The American Society for Pharmacology and Experimental Therapeutics, U.S.A.
Von Bebenburg, Von Walter, et al., "Über substituierte Polyaminopyridine", Chemiker-Zeitung, 1979, pp. 387-399, vol. 103, No. 12, Jahrgang, Germany.

* cited by examiner

*Primary Examiner*—Deepak Rao
(74) *Attorney, Agent, or Firm*—Stephen G. Kalinchak

(57) ABSTRACT

The present invention relates to pyrimidine derivatives of the general formula I or salts thereof

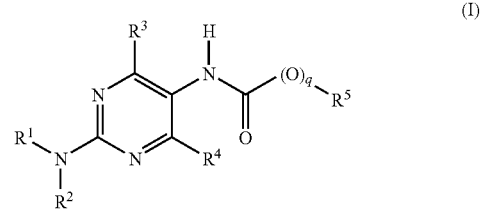

and their use.

5 Claims, No Drawings

SUBSTITUTED PYRIMIDINE DERIVATIVES

This application claims the benefit of priority under 35 U.S.C. §119(e) of U.S. Provisional Application No. 60/715,988, filed Sep. 9, 2005, and claims the benefit of priority under 35 U.S.C. §119(a)-(d) of Danish Application No. PA 2005 01262 filed Sep. 9, 2005, the contents of which are hereby incorporated by reference into the subject application.

FIELD OF THE INVENTION

The present invention relates to compounds, which are openers of the KCNQ family potassium ion channels. The compounds are useful in the treatment of disorders and diseases being responsive to opening of the KCNQ family potassium ion channels, one such disease is epilepsy.

BACKGROUND OF THE INVENTION

Ion channels are cellular proteins that regulate the flow of ions, including potassium, calcium, chloride and sodium into and out of cells. Such channels are present in all animal and human cells and affect a variety of processes including neuronal transmission, muscle contraction and cellular secretion.

Humans have over 70 genes encoding potassium channel subtypes (Jentsch *Nature Reviews Neuroscience* 2000, 1, 21-30) with a great diversity with regard to both structure and function. Neuronal potassium channels, which are found in the brain, are primarily responsible for maintaining a negative resting membrane potential, as well as controlling membrane repolarisation following an action potential.

One subset of potassium channel genes is the KCNQ family. Mutations in four out of five KCNQ genes have been shown to underlie diseases including cardiac arrhythmias, deafness and epilepsy (Jentsch *Nature Reviews Neuroscience* 2000, 1, 21-30).

The KCNQ4 gene is thought to encode the molecular correlate of a potassium channel found in outer hair cells of the cochlea and in Type I hair cells of the vestibular apparatus, in which mutations can lead to a form of inherited deafness.

KCNQ1 (KvLQT1) is co-assembled with the product of the KCNE1 (minimal K(+)-channel protein) gene in the heart to form a cardiac-delayed rectifier-like K(+) current. Mutations in this channel can cause one form of inherited long QT syndrome type 1 (LQT1), as well as being associated with a form of deafness (Robbins *Pharmacol Ther* 2001, 90, 1-19).

The genes KCNQ2 and KCNQ3 were discovered in 1988 and appear to be mutated in an inherited form of epilepsy known as benign familial neonatal convulsions (Rogawski *Trends in Neurosciences* 2000, 23, 393-398). The proteins encoded by the KCNQ2 and KCNQ3 genes are localised in the pyramidal neurons of the human cortex and hippocampus, regions of the brain associated with seizure generation and propagation (Cooper et al. *Proceedings National Academy of Science USA* 2000, 97, 4914-4919).

KCNQ2 and KCNQ3 are two potassium channel subunits that form "M-currents" when expressed in vitro. The M-current is a non-inactivating potassium current found in many neuronal cell types. In each cell type it is dominant in controlling membrane excitability by being the only sustained current in the range of action potential initiation (Marrion *Annual Review Physiology* 1997, 59, 483-504). Modulation of the M-current has dramatic effects on neuronal excitability, for example activation of the current will reduce neuronal excitability. Openers of these KCNQ channels, or activators of the M-current, will reduce excessive neuronal activity and may thus be of use in the treatment of seizures and other diseases and disorders characterised by excessive neuronal activity, such as neuronal hyperexcitability including convulsive disorders, epilepsy and neuropathic pain.

Retigabine (D-23129; N-(2-amino-4-(4-fluorobenzylamino)-phenyl)carbamic acid ethyl ester) and analogues thereof are disclosed in EP554543. Retigabine is an anticonvulsive compound with a broad spectrum and potent anticonvulsant properties, both in vitro and in vivo. It is active after oral and intraperitoneal administration in rats and mice in a range of anticonvulsant tests including: electrically induced seizures, seizures induced chemically by pentylenetetrazole, picrotoxin and N-methyl-D-aspartate (NMDA) and in a genetic animal model, the DBA/2 mouse (Rostock et al. *Epilepsy Research* 1996, 23, 211-223). In addition, retigabine is active in the amygdala kindling model of complex partial seizures, further indicating that this compound has potential for anti-convulsive therapy. In clinical trials, retigabine has recently shown effectiveness in reducing the incidence of seizures in epileptic patients (Bialer et al. *Epilepsy Research* 2002, 51, 31-71).

Retigabine has been shown to activate a K(+) current in neuronal cells and the pharmacology of this induced current displays concordance with the published pharmacology of the M-channel, which recently was correlated to the KCNQ2/3 K(+) channel heteromultimer. This suggests that activation of KCNQ2/3 channels may be responsible for some of the anticonvulsant activity of this agent (Wickenden et al. *Molecular Pharmacology* 2000, 58, 591-600)—and that other agents working by the same mechanism may have similar uses.

KCNQ 2 and 3 channels have also been reported to be upregulated in models of neuropathic pain (Wickenden et al. *Society for Neuroscience Abstracts* 2002, 454.7), and potassium channel modulators have been hypothesised to be active in both neuropathic pain and epilepsy (Schroder et al. *Neuropharmacology* 2001, 40, 888-898).

Retigabine has also been shown to be beneficial in animal models of neuropathic pain (Blackburn-Munro and Jensen *European Journal of Pharmacology* 2003, 460, 109-116), and it is thus suggested that openers of KCNQ channels will be of use in treating pain disorders including neuropathic pain.

The localisation of KCNQ channel mRNA is reported in brain and other central nervous system areas associated with pain (Goldstein et al. *Society for Neuroscience Abstracts* 2003, 53.8).

In addition to a role in neuropathic pain, the expression of mRNA for KCNQ 2-5 in the trigeminal and dorsal root ganglia and in the trigeminal nucleus caudalis implies that openers of these channels may also affect the sensory processing of migraine pain (Goldstein et al. *Society for Neuroscience Abstracts* 2003, 53.8).

Recent reports demonstrate that mRNA for KCNQ 3 and 5, in addition to that for KCNQ2, are expressed in astrocytes and glial cells. Thus KCNQ 2, 3 and 5 channels may help modulate synaptic activity in the CNS and contribute to the neuroprotective effects of KCNQ channel openers (Noda et al., *Society for Neuroscience Abstracts* 2003, 53.9).

Retigabine and other KCNQ modulators may thus exhibit protection against the neurodegenerative aspects of epilepsy, as retigabine has been shown to prevent limbic neurodegeneration and the expression of markers of apoptosis following kainic acid-induced status epilepticus in the rat (Ebert et al. *Epilepsia* 2002, 43 Suppl 5, 86-95). This may have relevance for preventing the progression of epilepsy in patients, i.e. be anti-epileptogenic. Retigabine has also been shown to delay the progression of hippocampal kindling in the rat, a further model of epilepsy development (Tober et al. *European Journal Of Pharmacology* 1996, 303, 163-169).

It is thus suggested that these properties of retigabine and other KCNQ modulators may prevent neuronal damage induced by excessive neuronal activation, and such compounds may be of use in the treatment of neurodegenerative diseases, and be disease modifying (or antiepileptogenic) in patients with epilepsy.

Given that anticonvulsant compounds such as benzodiazepines and chlormethiazole are used clinically in the treatment of the ethanol withdrawal syndrome and that other anticonvulsant compounds e.g. gabapentin are very effective in animal models of this syndrome (Watson et al. *Neuropharmacology* 1997, 36, 1369-1375), other anticonvulsant compounds such as KCNQ openers are thus expected to be effective in this condition.

mRNA for KCNQ 2 and 3 subunits are found in brain regions associated with anxiety and emotional behaviours such as bipolar disorder e.g. hippocampus and amygdala (Saganich et al. *Journal of Neuroscience* 2001, 21, 4609-4624), and retigabine is reportedly active in some animal models of anxiety-like behaviour (Hartz et al. *Journal of Psychopharmacology* 2003, 17 suppl 3, A28, B16), and other clinically used anticonvulsant compounds are used in the treatment of bipolar disorder. Thus, KCNQ openers may be useful for the treatment of anxiety disorders and bipolar disorder.

WO 200196540 discloses the use of modulators of the M-current formed by expression of KCNQ2 and KCNQ3 genes for insomnia, while WO 2001092526 discloses that modulators of KCNQ5 can be utilized for the treatment of sleep disorders.

WO01/022953 describes the use of retigabine for prophylaxis and treatment of neuropathic pain such as allodynia, hyperalgesic pain, phantom pain, neuropathic pain related to diabetic neuropathy and neuropathic pain related to migraine.

WO02/049628 describes the use of retigabine for the treatment of anxiety disorders such as anxiety, generalized anxiety disorder, panic anxiety, obsessive compulsive disorder, social phobia, performance anxiety, post-traumatic stress disorder, acute stress reaction, adjustment disorders, hypochondriacal disorders, separation anxiety disorder, agoraphobia and specific phobias.

WO97/15300 describes the use of retigabine for the treatment of neurodegenerative disorders such as Alzheimer's disease; Huntington's chorea; sclerosis such as multiple sclerosis and amyotrophic lateral sclerosis; Creutzfeld-Jakob disease; Parkinson's disease; encephalopathies induced by AIDS or infection by rubella viruses, herpes viruses, borrelia and unknown pathogens; trauma-induced neurodegenerations; neuronal hyperexcitation states such as in medicament withdrawal or intoxication; and neurodegenerative diseases of the peripheral nervous system such as polyneuropathies and polyneuritides.

KCNQ channel openers have also been found to be effective in the treatment of stroke, therefore it can be expected that selective KCNQ openers are effective in the treatment of stroke (Schroder et al., Pflugers Arch., 2003; 446(5): 607-16; Cooper and Jan, Arch Neurol., 2003, 60(4):496-500; Jensen, CNS Drug Rev., 2002, 8(4):353-60).

KCNQ channels have been shown to be expressed in dopaminergic and cholinergic circuits in the brain that are associated with the brain's reward system, particularly the ventral tegmental area (Cooper et al., J Neurosci, 2001, 21, 9529-9540). Therefore, KCNQ channel openers are expected to be effective in hyperexcitability disorders that involve the brain's reward system such as cocaine abuse, nicotine withdrawal and ethanol withdrawal.

Potassium channels comprised of the KCNQ4 subunits are expressed in the inner ear (Kubisch et al., Cell., 1999 Feb. 5; 96(3):437-46) and opening of these channels is therefore expected to treat tinnitus.

Hence, there is a great desire for novel compounds which are potent openers of the KCNQ family of potassium channels.

Also desired are novel compounds with improved properties relative to known compounds, which are openers of the KCNQ family potassium channels, such as retigabine. Improvement of one or more of the following parameters is desired:

half-life, clearance, selectivity, interactions with other medications, bioavailability, potency, formulability, chemical stability, metabolic stability, membrane permeability, solubility and therapeutic index. The improvement of such parameters may lead to improvements such as:

an improved dosing regime by reducing the number of required doses a day, ease of administration to patients on multiple medications, reduced side effects, enlarged therapeutic index, improved tolerability or improved compliance.

SUMMARY OF THE INVENTION

One object of the invention is the provision of compounds which are potent openers of the KCNQ family potassium channels.

The compounds of the invention are substituted pyrimidine derivatives of the below formula I or salts thereof

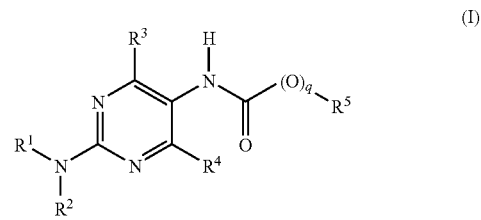

wherein $R^1$, $R^2$, $R^3$, $R^4$, $R^5$ and q are as defined below.

The invention provides a compound of formula I for use as a medicament.

The invention provides a pharmaceutical composition comprising a compound of formula I and a pharmaceutically acceptable carrier or diluent.

The invention provides the use of a compound of formula I for the preparation of a medicament for the treatment of seizure disorders, anxiety disorders, neuropathic pain and migraine pain disorders, other pain disorders, such as cancer pain, neurodegenerative disorders, stroke, cocaine abuse, nicotine withdrawal, ethanol withdrawal or hearing disorders, such as tinnitus.

The invention furthermore concerns the use of a compound of formula I in a method of treatment of seizure disorders, anxiety disorders, neuropathic pain and migraine pain disorders, other pain disorders, such as cancer pain, neurodegenerative disorders, stroke, cocaine abuse, nicotine withdrawal, ethanol withdrawal or hearing disorders, such as tinnitus.

DEFINITION OF SUBSTITUENTS

The term "heteroatom" refers to a nitrogen, oxygen or sulphur atom.

"Halogen" means fluoro, chloro, bromo or iodo. "Halo" means halogen.

"Cyano" designates

which is attached to the remainder of the molecule via the carbon atom.

"Amino" designates $NH_2$, which is attached to the remainder of the molecule via the nitrogen atom.

The expression "$C_{1-6}$-alk(en/yn)yl" means $C_{1-6}$-alkyl, $C_{2-6}$-alkenyl or $C_{2-6}$-alkynyl.

The term "$C_{1-6}$-alkyl" refers to a branched or unbranched alkyl group having from one to six carbon atoms, including but not limited to methyl, ethyl, prop-1-yl, prop-2-yl, 2-methyl-prop-1-yl, 2-methyl-prop-2-yl, 2,2-dimethyl-prop-1-yl, but-1-yl, but-2-yl, 3-methyl-but-1-yl, 3-methyl-but-2-yl, pent-1-yl, pent-2-yl, pent-3-yl, hex-1-yl, hex-2-yl and hex-3-yl. The term "$C_{2-6}$-alkenyl" refers to a branched or unbranched alkenyl group having from two to six carbon atoms and one double bond, including but not limited to ethenyl, propenyl and butenyl.

The term "$C_{2-6}$-alkynyl" refers to a branched or unbranched alkynyl group having from two to six carbon atoms and one triple bond, including but not limited to ethynyl, propynyl and butynyl.

The expression "$C_{1-10}$-alk(en/yn)yl" means $C_{1-10}$-alkyl, $C_{2-10}$-alkenyl or $C_{2-10}$-alkynyl. The term "$C_{1-10}$-alkyl" refers to a branched or unbranched alkyl group having from one to ten carbon atoms, including but not limited to methyl, ethyl, prop-1-yl, prop-2-yl, 2-methyl-prop-1-yl, 2-methyl-prop-2-yl, 2,2-dimethyl-prop-1-yl, but-1-yl, but-2-yl, 3-methyl-but-1-yl, 3-methyl-but-2-yl, pent-1-yl, pent-2-yl, pent-3-yl, hex-1-yl, hex-2-yl, hex-3-yl, 2-methyl-4,4-dimethyl-pent-1-yl and hept-1-yl.

The term "$C_{2-10}$-alkenyl" refers to a branched or unbranched alkenyl group having from two to ten carbon atoms and one double bond, including but not limited to ethenyl, propenyl and butenyl.

The term "$C_{2-10}$-alkynyl" refers to a branched or unbranched alkynyl group having from two to ten carbon atoms and one triple bond, including but not limited to ethynyl, propynyl and butynyl.

The expression "$C_{3-8}$-cycloalk(en)yl" means $C_{3-8}$-cycloalkyl or $C_{3-8}$-cycloalkenyl.

The term "$C_{3-8}$-cycloalkyl" designates a monocyclic or bicyclic carbocycle having three to eight carbon atoms, including but not limited to cyclopropyl, cyclopentyl, cyclohexyl, bicycloheptyl such as 2-bicyclo[2.2.1]heptyl.

The term "$C_{3-8}$-cycloalkenyl" designates a monocyclic or bicyclic carbocycle having three to eight carbon atoms and one double bond, including but not limited to cyclopentenyl and cyclohexenyl.

The term "halo-$C_{1-6}$-alk(en/yn)yl" designates $C_{1-6}$-alk(en/yn)yl being substituted with halogen, including but not limited to trifluoromethyl.

The term "halo-$C_{1-6}$-alk(en/yn)yloxy" designates $C_{1-6}$-alk(en/yn)yloxy being substituted with halogen, including but not limited to trifluoromethyloxy.

Similarly, "halo-$C_{3-8}$-cycloalk(en)yl" designates $C_{3-8}$-cycloalk(en)yl being substituted with halogen, including but not limited to chlorocyclopropane and chlorocyclohexane.

Similarly, "halo-$C_{3-8}$-cycloalk(en)yloxy" designates $C_{3-8}$-cycloalk(en)yloxy being substituted with halogen, including but not limited to chlorocyclopropyloxy and chlorocyclohexyloxy.

Similarly, "halo-$C_{3-8}$-cycloalk(en)yl-$C_{1-6}$-alk(en/yn)yloxy" designates halo-$C_{3-8}$-cycloalk(en)yl being attached to the remainder of the molecule via $C_{1-6}$-alk(en/yn)yloxy.

The term "$C_{1-6}$-alk(en/yn)yloxy" designates $C_{1-4}$-alk(en/yn)yl being attached to the remainder of the molecule via an oxygen atom.

Similarly, "$C_{3-8}$-cycloalk(en)yloxy" designates $C_{3-8}$-cycloalk(en)yl being attached to the remainder of the molecule via an oxygen atom.

The term "aryl" designates monocyclic or bicyclic aromatic systems being selected from the group consisting of phenyl, naphthyl, thiophen, furan, benzothiophen and benzofuran.

The term "optionally substituted aryl-$C_{1-6}$-alk(en/yn)yl" designates aryl-$C_{1-6}$-alk(en/yn)yl wherein the aryl moiety is optionally substituted, such as with 1, 2 or 3 substituents independently selected from the group consisting of halogen, cyano, $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$alk(en/yn)yl, $C_{1-6}$-alk(en/yn)yloxy, $C_{3-8}$-cycloalk(en)yloxy and $C_{3-8}$-cycloalk(en)yl-$C_{1-6}$-alk(en/yn)yloxy.

Similarly, "optionally substituted aryl" designates aryl wherein the aryl is optionally substituted, such as with 1, 2 or 3 substituents independently selected from the group consisting of halogen, cyano, $C_{1-6}$-alk(en/yn)yl, $C_{3-8}$-cycloalk(en)yl, $C_{3-8}$-cycloalk(en)yl-$C_{6}$-alk(en/yn)yl, halo-$C_{1-6}$-alk(en/yn)yl, halo-$C_{3-8}$-cycloalk(en)yl, halo-$C_{3-8}$-cycloalk(en)yl-$C_{1-6}$-alk(en/yn)yl, $C_{1-6}$-alk(en/yn)yloxy, $C_{3-8}$-cycloalk(en)yloxy and $C_{3-8}$-cycloalk(en)yl-$C_{1-6}$-alk(en/yn)yloxy.

In the expressions "$C_{3-8}$-cycloalk(en)yl-$C_{1-6}$alk(en/yn)yl", "aryl-$C_{1-6}$-alk(en/yn)yl" and "$C_{3-8}$-cycloalk(en)yl-$C_{1-6}$-alk(en/yn)yloxy", the terms "$C_{1-6}$alk(en/yn)yl", "$C_{3-8}$-cycloalk(en)yl", "aryl" and "$C_{1-6}$-alk(en/yn)yloxy" are as defined above.

DESCRIPTION OF THE INVENTION

The present invention relates to substituted pyrimidine derivatives which are potent openers of KCNQ potassium channels.

The present invention relates to a compound represented by the general formula I or salts thereof:

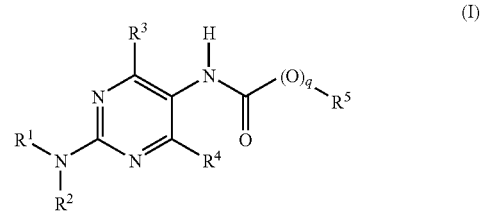

(I)

wherein: q is 0 or 1;

$R^1$ and $R^2$ are independently selected from the group consisting of hydrogen and optionally substituted aryl-$C_{1-6}$-alk(en/yn)yl, provided that $R^1$ and $R^2$ are not both hydrogen, or $R^1$ and $R^2$ together with the nitrogen to which they are attached form a 5 to 7 membered ring optionally containing a further heteroatom;

$R^3$ and $R^4$ are independently selected from hydrogen, halogen, cyano, amino, $C_{1-6}$-alk(en/yn)yl, $C_{3-8}$-cycloalk(en)yl, halo-$C_{1-6}$-alk(en/yn)yl, halo-$C_{3-8}$-cycloalk(en)yl, $C_{1-6}$-alk(en/yn)yloxy, $C_{3-8}$-cycloalk(en)yloxy, $C_{3-8}$-cycloalk(en)yl-$C_{1-6}$-alk(en/yn)yloxy, halo-$C_{1-6}$-alk(en/yn)yloxy, halo-$C_{3-8}$-cycloalk(en)yloxy and halo-$C_{3-8}$-cycloalk(en)yl-$C_{1-6}$-alk(en/yn)yloxy, provided that $R^3$ and $R^4$ are not both hydrogen;

$R^5$ is selected from the group consisting of $C_{1-10}$-alk(en/yn)yl, $C_{3-8}$-cycloalk(en)yl-$C_{1-6}$-alk(en/yn)yl, optionally substituted aryl-$C_{1-6}$-alk(en/yn)yl and optionally substituted aryl;

In one embodiment of the compound of formula I, q is 0.
In another embodiment of the compound of formula I, q is 1.

In a further embodiment of the compound of formula I $R^1$ and $R^2$ are independently selected from hydrogen and optionally substituted aryl-$C_{1-6}$-alk(en/yn)yl, provided that $R^1$ and $R^2$ are not both hydrogen.

In a further embodiment of the compound of formula I $R^1$ and $R^2$ together with the nitrogen to which they are attached form a 5 to 7 membered ring optionally containing a further hetero atom; in another embodiment said further hetero atom is oxygen; in another embodiment said ring is a 6 membered ring; in another embodiment said ring is a morpholine ring.

In a further embodiment of the compound of formula I $R^3$ and $R^4$ are independently selected from amino and $C_{1-6}$-alk(en/yn)yl, preferably methyl.

In a further embodiment of the compound of formula I $R^5$ is selected from the group consisting of $C_{1-10}$-alk(en/yn)yl, $C_{3-8}$-cycloalk(en)yl-$C_{1-6}$-alk(en/yn)yl, optionally substituted aryl-$C_{1-6}$-alk(en/yn)yl and optionally substituted aryl.

A further embodiment concerns a compound of formula I as the free base or a salt thereof, said compound is selected from the compounds of the following scheme:

Example No. Name
1a  N-[4-Amino-6-methyl-2-(4-trifluoromethylbenzylamino)-pyrimidin-5-yl]-2-cyclopentylacetamide
1b  N-[4-Amino-6-methyl-2-(4-trifluoromethylbenzylamino)-pyrimidin-5-yl]-3,3-dimethylbutyramide
1c  N-[4-Amino-6-methyl-2-(4-trifluoromethylbenzylamino)-pyrimidin-5-yl]-2-(4-fluorophenyl)-acetamide
1d Hexanoic acid [4-amino-6-methyl-2-(4-trifluoromethylbenzylamino)-pyrimidin-5-yl]-amide
1e  N-[4-Amino-6-methyl-2-(4-trifluoromethylbenzylamino)-pyrimidin-5-yl]-2-(3-chlorophenyl)-acetamide
2a 2-Cyclopentyl-N-(4,6-dimethyl-2-morpholin-4-yl-pyrimidin-5-yl)-acetamide
2b N-(4,6-Dimethyl-2-morpholin-4-yl-pyrimidin-5-yl)-3,3-dimethylbutyramide
2c N-(4,6-Dimethyl-2-morpholin-4-ylpyrimidin-5-yl)-2-(4-fluorophenyl)-acetamide
2d 2-(3,4-Difluorophenyl)-N-(4,6-dimethyl-2-morpholin-4-ylpyrimidin-5-yl)-acetamide
2e N-(4,6-Dimethyl-2-morpholin-4-ylpyrimidin-5-yl)-2-(3-fluorophenyl)-acetamide
2f Hexanoic acid (4,6-dimethyl-2-morpholin-4-ylpyrimidin-5-yl)-amide Each of these compounds is considered a specific embodiment and may be subjected to individual claims.

The present invention also comprises salts of the compounds of the invention, typically, pharmaceutically acceptable salts. The salts of the invention include acid addition salts, metal salts, ammonium and alkylated ammonium salts.

The salts of the invention are preferably acid addition salts. The acid addition salts of the invention are preferably pharmaceutically acceptable salts of the compounds of the invention formed with non-toxic acids. Acid addition salts include salts of inorganic acids as well as organic acids. Examples of suitable inorganic acids include hydrochloric, hydrobromic, hydroiodic, phosphoric, sulfuric, sulfamic, nitric acids and the like. Examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutical acceptable inorganic or organic acid addition salts include the pharmaceutically acceptable salts listed in J. Pharm. Sci. 1977,66,2, which is incorporated herein by reference.

Also intended as acid addition salts are the hydrates, which the present compounds are able to form.

Examples of metal salts include lithium, sodium, potassium, magnesium salts and the like.

Examples of ammonium and alkylated ammonium salts include ammonium, methyl-, dimethyl-, trimethyl-, ethyl-, hydroxyethyl-, diethyl-, n-butyl-, sec-butyl-, tert-butyl-, tetramethylammonium salts and the like.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

The compounds of the present invention may have one or more asymmetric centre and it is intended that any optical isomers (i.e. enantiomers or diastereomers), as separated, pure or partially purified optical isomers and any mixtures thereof including racemic mixtures, i.e. a mixture of stereoisomers, are included within the scope of the invention.

Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can also be resolved into their optical antipodes, e.g. by fractional crystallization. The compounds of the present invention may also be resolved by the formation of diastereomeric derivatives. Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981). Optically active compounds can also be prepared from optically active starting materials or by stereoselective synthesis.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

The invention also encompasses prodrugs of the present compounds, which on administration undergo chemical conversion by metabolic processes before becoming pharmacologically active substances. In general, such prodrugs will be functional derivatives of the compounds of the general formula I, which are readily convertible in vivo into the required compound of the formula I. Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The compounds according to the invention have affinity for the KCNQ2 receptor subtype with an $EC_{50}$ of less than 15000 nM such as less than 10000 nM as measured by the test "Relative efflux through the KCNQ2 channel" which is described below. One embodiment concerns such compounds of formula I having affinity for the KCNQ2 receptor subtype with an $EC_{50}$ of less than 200 nM such as less than 1500 nM as measured by the test "Relative efflux through the KCNQ2 channel" which is described below. To further illustrate without limiting the invention an embodiment concerns such compounds having affinity for the KCNQ2 receptor subtype with an $EC_{50}$ of less than 200 nM such as less than 150 nM as measured by the test "Relative efflux through the KCNQ2 channel" which is described below.

One embodiment concerns such compounds of formula I having an $ED_{50}$ of less than 15 mg/kg in the test "Maximum electroshock" which is described below. To further illustrate without limiting the invention an embodiment concerns such compounds having an $ED_{50}$ of less than 5 mg/kg in the test "Maximum electroshock" which is described below.

One embodiment concerns such compounds of formula I having an $ED_{50}$ of less than 5 mg/kg in the "Electrical seizure-threshold test" and "Chemical seizure-threshold test" which is described below.

One embodiment concerns such compounds of formula I having few or clinically insignificant side effects. Some of the compounds according to the invention are thus tested in models of the unwanted sedative, hypothermic and ataxic actions.

One embodiment concerns such compounds of formula I having a large therapeutic index between anticonvulsant efficacy and side-effects such as impairment of locomotor activity or ataxic effects as measured by performance on a rotating rod. Such compounds will expectedly be well tolerated in patients permitting high doses to be used before side effects are seen. Thereby compliance with the therapy will expectedly be good and administration of high doses may be permitted making the treatment more efficacious in patients who would otherwise have side effects with other medications.

As already mentioned, the compounds according to the invention have effect on potassium channels of the KCNQ family, in particular the KCNQ2 subunit, and they are thus considered useful for increasing ion flow in a voltage-dependent potassium channel in a mammal such as a human. The compounds of the invention are considered applicable in the treatment of a disorder or disease being responsive to an increased ion flow in a potassium channel such as the KCNQ family potassium ion channels. Such disorder or disease is preferably a disorder or disease of the central nervous system.

In one aspect, the compounds of the invention may be administered as the only therapeutically effective compound.

In another aspect the compounds of the invention may be administered as a part of a combination therapy, i.e. the compounds of the invention may be administered in combination with other therapeutically effective compounds having e.g. anti-convulsive properties. The effects of such other compounds having anti-convulsive properties may include but not be limited to activities on:

ion channels such as sodium, potassium, or calcium channels the excitatory amino acid systems e.g. blockade or modulation of NMDA receptors the inhibitory neurotransmitter systems e.g. enhancement of GABA release, or blockade of GABA-uptake or membrane stabilisation effects.

Current anti-convulsive medications include, but are not limited to, tiagabine, carbamazepine, sodium valproate, lamotrigine, gabapentin, pregabalin, ethosuximide, levetiracetam, phenyloin, topiramate, zonisamide as well as members of the benzodiazepine and barbiturate class.

An aspect of the invention provides a compound of formula I or a salt thereof for use as a medicament.

In one embodiment, the invention relates to the use of a compound of formula I or a salt thereof in a method of treatment.

An embodiment of the invention provides a pharmaceutical composition comprising a compound of formula I or a salt thereof and one or more pharmaceutically acceptable carrier or diluent. The composition may comprise any of the embodiments of formula I as described above.

A further embodiment of the invention relates to the use of a compound of formula I or a salt thereof for increasing ion flow in a potassium channel of a mammal such as a human.

A further embodiment of the invention relates to the use of a compound of formula I or a salt thereof for the treatment of a disorder or disease being responsive to an increased ion flow in a potassium channel, such disorder or disease is preferably a disorder or disease of the central nervous system.

A further embodiment of the invention relates to the use of a compound of formula I or a salt thereof for the preparation of a pharmaceutical composition for the treatment of a disease or disorder wherein a KCNQ potassium channel opener such as a KCNQ2 potassium channel opener is beneficial. Typically, such disorder or disease is selected from the group consisting of seizure disorders, anxiety disorders, neuropathic pain and migraine pain disorders, other pain disorders, such as cancer pain, neurodegenerative disorders, stroke, cocaine abuse, nicotine withdrawal, ethanol withdrawal or hearing disorders, such as tinnitus.

A further embodiment of the invention relates to the use of a compound of formula I or a salt thereof for the preparation of a pharmaceutical composition for the treatment of seizure disorders.

Typically, the seizure disorders to be treated are selected from the group consisting of acute seizures, convulsions, status epilepticus and epilepsy such as epileptic syndromes and epileptic seizures.

A further embodiment of the invention relates to the use of a compound of formula I or a salt thereof for the preparation of a pharmaceutical composition for the treatment of anxiety disorders.

Typically, the anxiety disorders to be treated are selected from the group consisting of anxiety and disorders and diseases related to panic attack, agoraphobia, panic disorder with agoraphobia, panic disorder without agoraphobia, agoraphobia without history of panic disorder, specific phobia, social phobia and other specific phobias, obsessive-compulsive disorder, posttraumatic stress disorder, acute stress disorders, generalized anxiety disorder, anxiety disorder due to general medical condition, substance-induced anxiety disorder, separation anxiety disorder, adjustment disorders, performance anxiety, hypochondriacal disorders, anxiety disorder due to general medical condition and substance-induced anxiety disorder and anxiety disorder not otherwise specified.

A further embodiment of the invention relates to the use of a compound of formula I or a salt thereof for the preparation of a pharmaceutical composition for the treatment of neuropathic pain and migraine pain disorders.

Typically, the neuropathic pain and migraine pain disorders to be treated are selected from the group consisting of allodynia, hyperalgesic pain, phantom pain, neuropathic pain related to diabetic neuropathy, neuropathic pain related to trigeminal neuralgia and neuropathic pain related to migraine.

A further embodiment of the invention relates to the use of a compound of formula I or a salt thereof for the preparation of a pharmaceutical composition for the treatment of neurodegenerative disorders.

Typically the neurodegenerative disorders to be treated are selected from the group consisting of Alzheimer's disease, Huntington's chorea, multiple sclerosis, amyotrophic lateral sclerosis, Creutzfeld-Jakob disease, Parkinson's disease, encephalopathies induced by AIDS or infection by rubella viruses, herpes viruses, borrelia and unknown pathogens, trauma-induced neurodegenerations, neuronal hyperexcitation states such as in medicament withdrawal or intoxication and neurodegenerative diseases of the peripheral nervous system such as polyneuropathies and polyneuritides.

A further embodiment of the invention relates to the use of a compound of formula I or a salt thereof for the preparation of a pharmaceutical composition for the treatment of bipolar disorders or attention deficit hyperactivity disorder.

A further embodiment of the invention relates to the use of a compound of formula I or a salt thereof for the preparation of a pharmaceutical composition for the treatment of sleep disorders; such as insomnia.

A further embodiment of the invention relates to the use of a compound of formula I or a salt thereof for the preparation of a pharmaceutical composition for the treatment of fibromyalgia, a motor disorder or motion disorder, spasms, myokymia or urinary incontinence.

A further embodiment of the invention relates to the use of a compound of formula I or a salt thereof for the preparation of a pharmaceutical composition for the treatment of stroke, cocaine abuse, nicotine withdrawal, ethanol withdrawal or hearing disorders, such as tinnitus.

The term "treatment" as used herein in connection with a disease or disorders includes also prevention, inhibition and amelioration as the case may be.

The invention provides compounds showing effect in one or more of the following tests:

"Relative efflux through the KCNQ2 channel"

Which is a measure of the potency of the compound at the target channel

"Maximum electroshock"

Which is a measure of seizures induced by non-specific CNS stimulation by electrical means "Pilocarpine induced seizures"

Seizures induced by pilocarpine are often difficult to treat with many existing antiseizure medications and so reflect a model of "drug resistant seizures"

"Electrical seizure-threshold tests" and "Chemical seizure-threshold tests"

These models measure the threshold at which seizures are initiated, thus being models that detect whether compounds could delay seizure initiation.

"Amygdala kindling"

Which is used as a measure of disease progression, as in normal animals the seizures in this model get more severe as the animal receives further stimulations.

Pharmaceutical Compositions

The present invention also relates to a pharmaceutical composition. The compounds of the invention or salts thereof may be administered alone or in combination with pharmaceutically acceptable carriers or diluents, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19 Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the disorder or disease to be treated and the active ingredient chosen.

The pharmaceutical compositions formed by combining the compound of the invention and the pharmaceutical acceptable carriers are then readily administered in a variety of dosage forms suitable for the disclosed routes of administration. The formulations may conveniently be presented in unit dosage form by methods known in the art of pharmacy.

The compounds of this invention are generally utilized as the free substance or as a pharmaceutically acceptable salt thereof. One example is an acid addition salt of a compound having the utility of a free base. When a compound of the invention contains a free base such salts are prepared in a conventional manner by treating a solution or suspension of a free base of the invention with a chemical equivalent of a pharmaceutically acceptable acid. Representative examples are mentioned above.

Pharmaceutical compositions for oral administration may be solid or liquid. Solid dosage forms for oral administration include e.g. capsules, tablets, dragees, pills, lozenges, powders, granules and tablette e.g. placed in a hard gelatine capsule in powder or pellet form or e.g. in the form of a troche or lozenge. Where appropriate, pharmaceutical compositions for oral administration may be prepared with coatings such as enteric coatings or they can be formulated so as to provide controlled release of the active ingredient such as sustained or prolonged release according to methods well known in the art. Liquid dosage forms for oral administration include e.g. solutions, emulsions, suspensions, syrups and elixirs.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid, lower alkyl ethers of cellulose, corn starch, potato starch, gums and the like. Examples of liquid carriers are syrup, peanut oil, olive oil, phospho lipids, fatty acids, fatty acid amines, polyoxyethylene and water.

The carrier or diluent may include any sustained release material known in the art, such as glyceryl monostearate or glyceryl distearate, alone or mixed with a wax.

Any adjuvants or additives usually used for such purposes such as colourings, flavourings, preservatives etc. may be used provided that they are compatible with the active ingredients.

The amount of solid carrier may vary but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

Tablets may be prepared by mixing the active ingredient with ordinary adjuvants or diluents and subsequently compressing the mixture in a conventional tabletting machine.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Depot injectable formulations are also contemplated as being within the scope of the present invention.

For parenteral administration, solutions of the compound of the invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Solutions for injections may be prepared by dissolving the active ingredient and possible additives in a part of the solvent for injection, preferably sterile water, adjusting the solution to the desired volume, sterilising the solution and filling it in suitable ampoules or vials. Any suitable additive conventionally used in the art may be added, such as tonicity agents, preservatives, antioxidants, etc.

Other suitable administration forms include suppositories, sprays, ointments, cremes, gels, inhalants, dermal patches, implants, etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the disorder or disease treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.01 to about 1000 mg, such as about 0.01 to 100 mg, preferably from about 0.05 to about 500 mg, and more preferred from about 0.5 mg to about 200 mg.

For parenteral routes such as intravenous, intrathecal, intramuscular and similar administration, typically doses are in the order of about half the dose employed for oral administration.

Typical examples of recipes for the formulation of the invention are as follows:

1) Tablets containing 5.0 mg of a compound of the invention calculated as the free base:

| | |
|---|---|
| Compound of the invention | 5.0 mg |
| Lactose | 60 mg |
| Maize starch | 30 mg |
| Hydroxypropylcellulose | 2.4 mg |
| Microcrystalline cellulose | 19.2 mg |
| Croscarmellose Sodium Type A | 2.4 mg |
| Magnesium stearate | 0.84 mg |

2) Tablets containing 0.5 mg of a compound of the invention calculated as the free base:

| | |
|---|---|
| Compound of the invention | 0.5 mg |
| Lactose | 46.9 mg |
| Maize starch | 23.5 mg |
| Povidone | 1.8 mg |
| Microcrystalline cellulose | 14.4 mg |
| Croscarmellose Sodium Type A | 1.8 mg |
| Magnesium stearate | 0.63 mg |

3) Syrup containing per millilitre:

| | |
|---|---|
| Compound of the invention | 25 mg |
| Sorbitol | 500 mg |
| Hydroxypropylcellulose | 15 mg |
| Glycerol | 50 mg |
| Methyl-paraben | 1 mg |
| Propyl-paraben | 0.1 mg |
| Ethanol | 0.005 mL |
| Flavour | 0.05 mg |
| Saccharin sodium | 0.5 mg |
| Water | ad 1 mL |

4) Solution for injection containing per millilitre:

| | |
|---|---|
| Compound of the invention | 0.5 mg |
| Sorbitol | 5.1 mg |
| Acetic Acid | 0.05 mg |
| Saccharin sodium | 0.5 mg |
| Water | ad 1 mL |

By the expression a compound of the invention is meant any one of the embodiments of formula I as described herein.

In a further aspect the present invention relates to a method of preparing a compound of the invention as described in the following.

Methods of Preparation of the Compounds of the Invention

The compounds of the invention of the general formula I, wherein $R^1$, $R^2$, $R^3$, $R^4$, $R^5$, and q are as defined above may be prepared by the methods as represented in the schemes and as described below.

In the compounds of the general formulae I-XX, $R^1$, $R^2$, $R^3$, $R^4$, $R^5$ and q are as defined under formula I.

For compounds which can exist as equilibrium between two or more tautomers, only one tautomer is represented in the schemes, although it may not be to the most stable tautomer. Such compounds include, but not limited to hydroxypyrimidines of the general formula IX, X, XVII, XVIII as well known to chemists skilled in the art.

Compounds of the general formulae II, III, VII, VIII, IX, X, XI, XIV, XVI, XVII, XIX and XX are either obtained from commercial sources, or prepared by standard methods known to chemists skilled in the art.

Compounds of the general formula IV (Scheme 1) can be obtained by reacting compounds of the general formula II with amines of the general formula III with or without the addition of bases, such as trialkyl amines, potassium or sodium carbonate, in a suitable solvent, such as acetonitrile, N,N-dimethylformamide or ethanol, at a suitable temperature, such as room temperature, reflux temperature or at higher temperature under microwave irradiation in a sealed vessel.

Compounds of the general formula V may be prepared from compounds of the general formula IV, by reducing the nitro group to an amino group, with suitable reducing agents such as zinc or iron powder in the presence of acid such as acetic acid or aqueous hydrochloric acid, or by hydrogen gas or ammonium formiate in the presence of a suitable hydrogenation catalyst such as palladium on activated carbon in suitable solvents such as methanol, ethanol, ethyl acetate or tetrahydrofuran, at suitable temperatures or under ultrasonic irradiation. Alternatively, tin(II) chloride or sodium dithionite can be used as reducing agents under conditions well known to chemists skilled in the art.

Compounds of the invention of the general formula I may be prepared by reacting compounds of the general formula V with suitable electrophilic reagents, such as, but not limited to, suitably substituted carboxylic acid fluorides, carboxylic acid chlorides, carboxylic acid bromides, carboxylic acid iodides, carboxylic acid anhydrides, activated esters, chloroformates, and with or without the addition of bases, such as pyridine, trialkyl amines, potassium carbonate, magnesium oxide or lithium-, sodium-, or potassium alcoholates, in a suitable solvent, such as ethyl acetate, dioxane, tetrahydrofuran, acetonitrile or diethyl ether, at suitable temperatures, such as room temperature, reflux temperature or at higher temperature in a sealed vessel under microwave irradiation. Activated esters and carboxylic acid anhydrides can be prepared from suitably substituted carboxylic acids under conditions known to chemists skilled in the art, for example as described by F. Albericio and L. A. Carpino, "Coupling reagents and activation" in *Methods in enzymology: Solid-phase peptide synthesis*, pp. 104-126, Academic Press, New York, 1997. Carboxylic acid halides can be prepared from suitably substituted carboxylic acids by activation with reagents such as, but not limited to, thionyl chloride, oxalyl chloride, phosphorus tribromide or phosphorus triiodide under conditions well known to chemists skilled in the art.

Scheme I

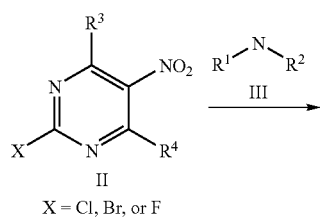

X = Cl, Br, or F

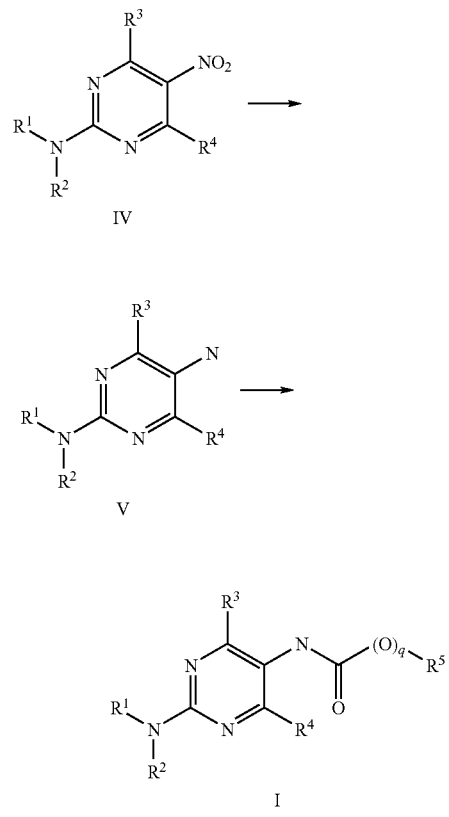

Compounds of the general formula II may be prepared as outlined in Scheme 2. Compounds of the general formula IX are prepared by condensation of urea with 1,3-dicarbonyl compounds VII or their equivalents such as unsaturated carbonyl compounds VIII in a suitable solvent such as N,N-dimethylformamide, N-methylpyrrolidinone or ethanol, with or without addition of catalyst such as hydrochloric, sulphuric, methansulfonic or polyphosphoric acids or Lewis acids at a suitable temperature, such as room temperature, reflux temperature or at higher temperature under microwave irradiation in a sealed vessel. Compounds of the general formula X may be prepared from compounds of the general formula IX, by nitration reactions known to chemists skilled in the art, such as reaction with concentrated nitric acid, sodium nitrite or sodium nitrate, in a suitable solvent, such as glacial acetic acid, acetic anhydride, trifluoroacetic acid, concentrated sulfuric acid or mixtures thereof, at appropriate temperatures, for example as described by P. B. D. de la Mare and J. H. Ridd, "Preparative methods of nitration" in *Aromatic substitutions*, pp. 48-56, Butterworths Scientific Publications, London, 1959. Compounds of the general formula X may be converted into compounds of the general formula II by methods known to chemists skilled in the art such chlorination or bromination reaction with phosphorus oxychloride or phosphorus oxybromide. Compounds of the general formula II, wherein X is fluorine or iodide, can be prepared from the compounds of the general formula II, wherein X is chloride or bromide, by halogen exchange reaction with appropriate reagents such as hydroiodic acid, hydrofluoric acid, sodium iodide, potassium fluoride under conditions known to chemists skilled in the art.

Scheme II

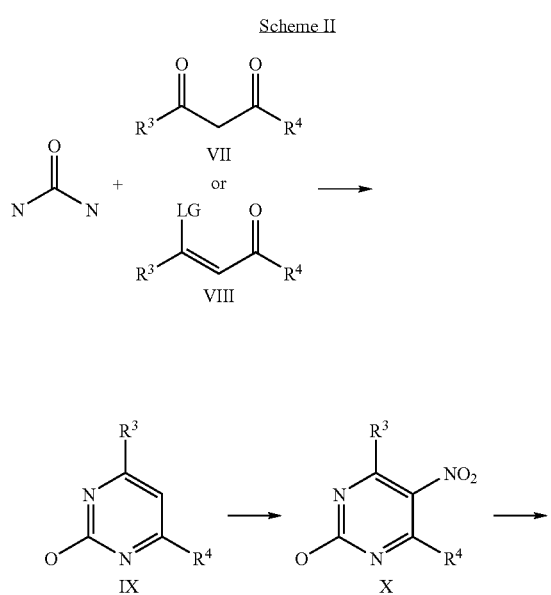

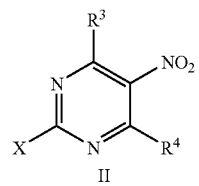

Compounds of the general formulae XII and XV (Scheme 3) may be prepared from appropriately substituted guanidines of the general formula XI by condensation reaction with 1,3-dicarbonyl compounds or their equivalent unsaturated carbonyl compounds of the general formulae VII, VIII (where LG is a suitable leaving group such as alkoxy or dialkylamino) or XIV under conditions as described under Scheme 2 for preparation of the compounds of the general formula IX. Compounds of the general formula XII can be converted into compounds of the general formula XV by diazo coupling well known to chemists skilled in the art. Alternatively, compounds of the general formula XV can be nitrated as described under Scheme 2 for the preparation of the compounds of the general formula X. Compounds of the general formula V may be prepared from compounds of the general formulae XIII or XV, by reducing the nitro group or diazo group, respectively, to an amino group, under condition as described above for the preparation of the compounds of the general formula V under Scheme 1.

Scheme 3

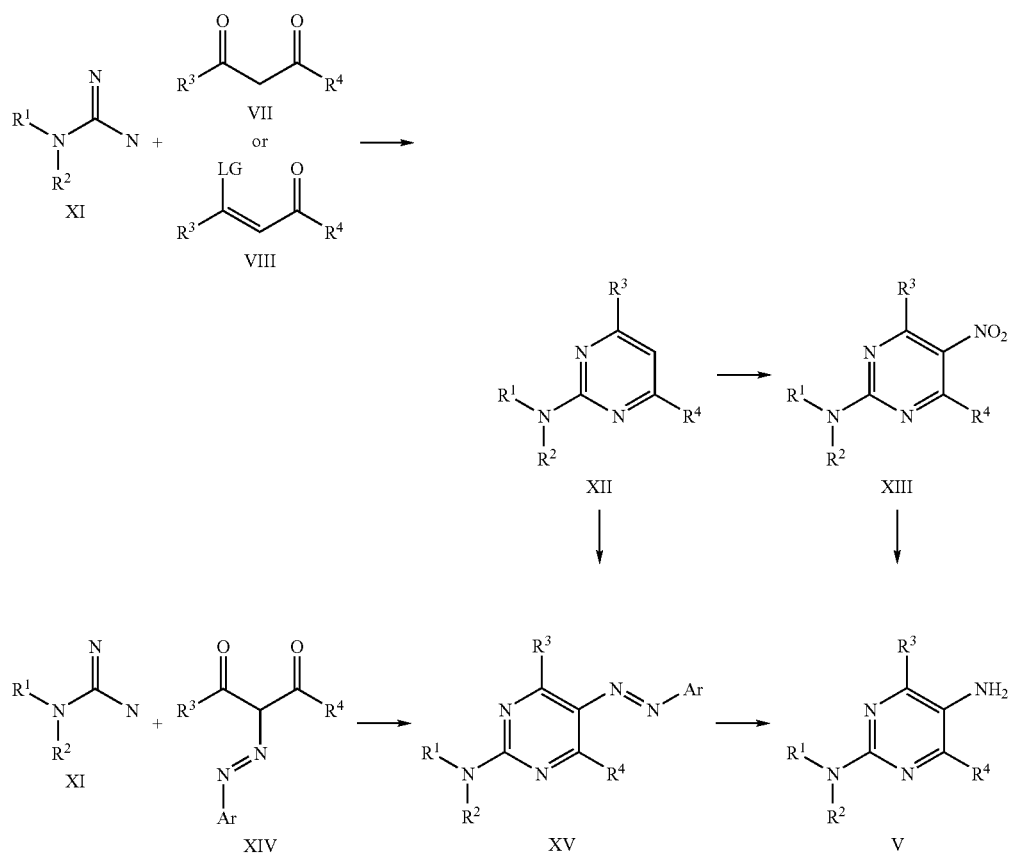

In particular, condensation of the substituted guanidines of the general formula XI with ketoesters or ketoacids of the general formula XVI (Scheme 4) under conditions described above under Scheme 3 may lead to formation of the compounds of the general formula XVII, which can be nitrated under conditions as described above to provide compounds of the general formula XVIII. The hydroxy group in XVIII may be converted to compounds of the general formula XX (XIII where $R^4$ is halogen) by halogenation reaction under condition as described above for preparation of compounds with the general formula II. Alternatively, compounds of the general formula XX (XIII where $R^4$ is halogen) may be prepared from the compounds of the general formula XIX (XIII where $R^4$ is amino) by diazotization reaction followed by nucleophilic substitution in the presence of the appropriate halogen anion under conditions well known to chemists skilled in the art. Compounds of the general formula XIII, wherein $R^4$ is $C_{1-6}$-alk(en/yn)yl, $C_{3-8}$-cycloalk(en)yl, $C_{3-8}$-cycloalk(en)yl-$C_{1-6}$-alk(en/yn)yl, halo-$C_{1-6}$-alk(en/yn)yl, halo-$C_{3-8}$-cycloalk(en)yl or halo-$C_{3-8}$-cycloalk(en)yl-$C_{1-6}$-alk(en/yn)yl, may be prepared from compounds of the general formula XX (XIII where $R^4$ is halogen) by means of cross-coupling reactions known to chemists skilled in the art, such as Negishi coupling (E.-I. Negishi, A. O. King and N. Okukado, *J. Org. Chem.*, 1977, 42, 1821), Sonogashira coupling (K. Sonogashira, Y. Tohda and N. Hagihara, *Tet. Lett.*, 1975, 16, 4467), or other transition metal catalyzed cross-coupling reactions such as copper catalyzed reactions (W. Dohle, D. M. Lindsay and P. Knochel, *Org. Lett.*, 2001, 3, 2871).

Additionally, compounds of the general formula XIII, wherein $R^4$ is cyano, may be prepared from compounds of the general formula XX (XIII where $R^4$ is halogen) by means of nickel-catalyzed cyanation reactions known to chemists skilled in the art for example as described by L. Cassar, *J. Organomet. Chem.*, 1973, 54, C57-C58.

Furthermore, compounds of the general formula XIII, wherein $R^4$ is $C_{1-6}$-alk(en/yn)yloxy, $C_{3-8}$-cycloalk(en)yloxy or $C_{3-8}$-cycloalk(en)yl-$C_{1-6}$-alk(en/yn)yloxy, may be prepared from compounds of general formula XX (XIII where $R^4$ is halogen) by reaction with the appropriate lithium-, sodium-, or potassium alcoholates or alcohols in the presence of base such as lithium-, sodium-, or potassium hydroxide, lithium-, sodium-, or potassium hydride, and with or without the addition of a catalyst such as copper sulfate, in a suitable solvent such as dioxane, at suitable temperatures, such as room temperature or reflux temperature.

Scheme 4

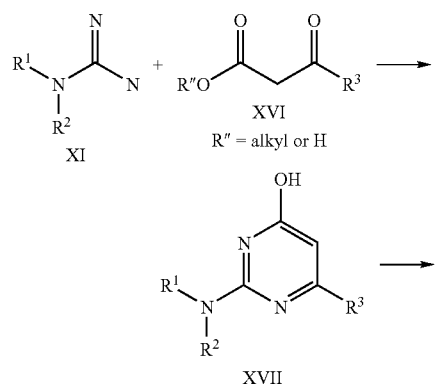

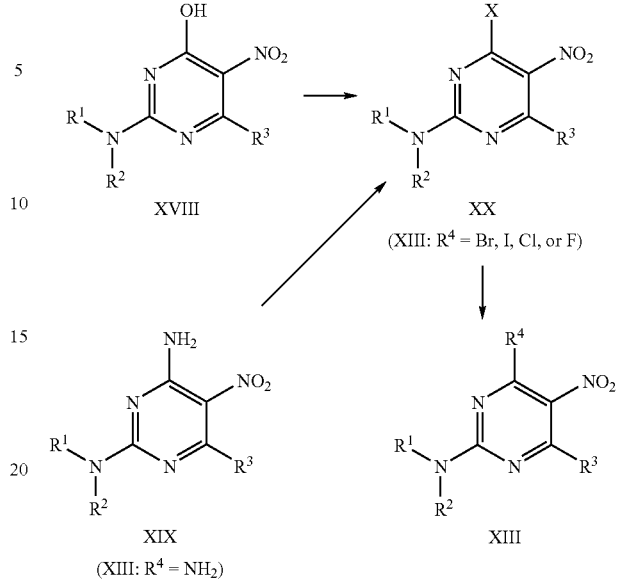

Alkynes prepared by Sonogashira reactions may be reduced to alkenes or alkanes by reduction with hydrogen gas or ammonium formiate in the presence of a suitable hydrogenation catalyst such as palladium on activated carbon or platinum on activated carbon in suitable solvents such as methanol, ethanol or tetrahydrofuran, at suitable temperatures for example as described by S. Siegel, "Heterogeneous catalytic hydrogenation of C=C and alkynes" in *Comprehensive Organic Synthesis*, v. 8, pp. 417-442, Pergamon Press, 1991.

Preparation of the Compounds of the Invention

EXAMPLES

Analytical LC-MS data were obtained on a PE Sciex API 150EX instrument equipped with atmospheric pressure photo ionisation and a Shimadzu LC-8A/SLC-10A LC system. Column: 30×4.6 mm Waters Symmetry C18 column with 3.5 µm particle size; Solventsystem: A=water/trifluoroacetic acid (100:0.05) and B=water/acetonitrile/trifluoroacetic acid (5:95:0.03); Method: Linear gradient elution with 90% A to 100% B in 4 minutes and with a flow rate of 2 mL/minute. The retention times ($t_R$) are expressed in minutes.

$^1$H NMR spectra were recorded at 500.13 MHz on a Bruker Avance DRX500 instrument. Deuterated dimethyl sulfoxide (99.8% D) was used as solvent. Tetramethylsilane was used as internal reference standard. Chemical shift values are expressed in ppm-values relative to tetramethylsilane. The following abbreviations are used for multiplicity of NMR signals: s=singlet, d=doublet, t=triplet, q=quartet, qui=quintet, h=heptet, dd=double doublet, ddd=double double doublet, dt=double triplet, dq=double quartet, tt=triplet of triplets, m=multiplet and br=broad singlet.

Microwave experiments were performed in sealed process vials or reactors using an Emrys Synthesizer or Emrys Optimizer EXP from Personal Chemistry or a Milestone Microsynth instrument from Milestone. When a reaction was heated in a microwave instrument, it was cooled to 25° C. before the next process step.

Preparation of Intermediates

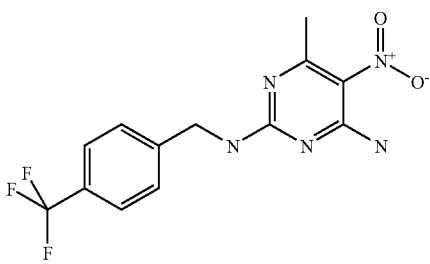

6-Methyl-5-nitro-N*2*-(4-trifluoromethylbenzyl)-pyrimidine-2,4-diamine

A mixture of 2-chloro-6-methyl-5-nitropyrimidin-4-ylamine (300 mg, 1.591 mmol), 4-trifluoromethylbenzylamine (369 mg, 2.107 mmol) in acetonitrile (3 ml) and triethylamine (0.5 ml) were flashed with argon, sealed in the Emrys process vial and heated at 120° C. for 2 min under microwave irradiation. The obtained suspension was quenched with 10% aqueous sodium carbonate (2 ml) and organic volatiles were evaporated under reduced pressure. Methanol (5 ml) and water (100 ml) were added to the residue. The product was separated by filtration, washed with water and dried in vacuo to give 490 mg of yellow solid. Yield 94%. LC-MS (m/z) 328.1 (MH$^+$); $t_R$=2.58. $^1$H NMR (500 MHz, DMSO-d$_6$): ca. 3:1 mixture of two rotamers, 2.54 (s, 3H), 4.57 (d, 1.5H), 4.63 (d, 0.5H), 7.52 (t, 2H), 7.68 (d, 2H), 7.81 (s, 0.5H, NH$_2$), 8.0 (s, 1.5H, NH$_2$), 8.17 (t, 0.25H, NH), 8.48 (t, 0.75H, NH).

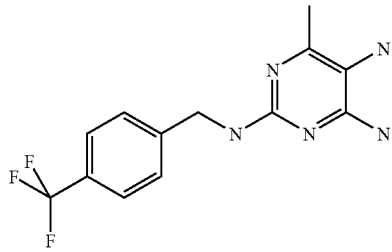

6-Methyl-N*2*-(4-trifluoromethylbenzyl)-pyrimidine-2,4,5-triamine

To a vigorously stirred solution of 6-methyl-5-nitro-N*2*-(4-trifluoromethylbenzyl)-pyrimidine-2,4-diamine (450 mg, 1.376 mmol) in tetrahydrofuran (20 ml) and acetic acid (5 ml) on cold water bath, zinc powder (particle size<10 micron, 5 g) was added by portions in 2 min. Water bath was removed and more zinc powder (2 g) were added. The suspension was stirred at ambient temperature for 60 min and quenched with 10% aqueous sodium carbonate to pH>8. The obtained suspension was extracted with ethyl acetate (10 times). The combined organic solution was filtered via plug of silica gel (10 g) and eluted with 20% in ethyl acetate to give 430 mg of pale yellow oil after evaporation. The product solidified after drying in vacuo. Yield 100%. It was used in the next step without further purification. LC-MS (m/z) 298.1 (MH$^+$); $t_R$=1.68. $^1$H NMR (500 MHz, DMSO-d$_6$): 2.02 (s, 3H), 3.1- 3.8 (br, NH$_2$+H$_2$O), 4.43 (d, 2H), 5.88 (br, 2H), 6.26 (t, 1H, NH), 7.48 (d, 2H), 7.62 (d, 2H).

3-Chlorophenylacetyl chloride

3-Chlorophenylacetic acid (19.7 g) in thionyl chloride (100 ml) was heated at reflux for 3 h.

Volatiles were removed in vacuo and the obtained oily residue was used in the next step without further purification. $^1$H NMR (500 MHz, CDCl$_3$): 4.12 (s, 2H), 7.16 (d, 1H), 7.27-7.34 (m, 3H).

The following acid chlorides were prepared analogously from corresponding acids:

3,4-Difluorophenylacetyl chloride $^1$H NMR (500 MHz, CDCl$_3$): 4.10 (s, 2H), 7.0 (m, 1H), 7.11 (ddd, 1H), 7.17 (dt, 1H).

3-Flurophenylacetyl chloride

The title compound was used in the next step without characterisation.

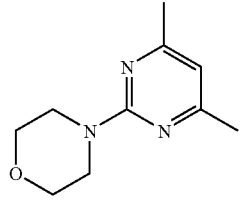

4-(4,6-Dimethyl-pyrimidin-2-yl)-morpholine

To a suspension of morpholinoformamidine hydrobromide (2.0 g, 9.52 mmol) in ethanol (6 ml) potassium tert-butoxide (1.068 g, 9.52 mmol) then acetylacetone (2 ml, 20 mmol) were added. The reaction mixture was flashed with argon, sealed in the Emrys process vial and heated under microwave irradiation at 140° C. for 5 min. After cooling it was quenched with ethyl acetate (50 ml), filtered via plug of SiO$_2$ (5 g) and eluted with ethyl acetate. Volatiles were removed in vacuo at 70° C. to furnish 1.65 g of pale brown oil that solidified overnight. Yield 90%. LC-MS (m/z) 193.9 (MH$^+$); $t_R$=0.71. $^1$H NMR (500 MHz, DMSO-d$_6$): 2.23 (s, 6H), 3.62 (m, 4H), 3.67 (m, 4H), 6.44 (s, 1H).

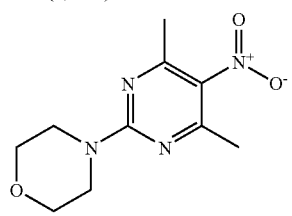

4-(4,6-Dimethyl-5-nitro-pyrimidin-2-yl)-morpholine

Method A. To a stirred solution of 4-(4,6-Dimethylpyrimidin-2-yl)-morpholine (8.94 g, 46.3 mmol) in glacial acetic acid (50 ml) fuming nitric acid (5.75 ml, 3 eq.) was added dropwise. The reaction mixture was heated at 70° C. for 15 min then more nitric acid (3.8 ml, 2 eq.) was added. After additional 15 min at 70° it was cooled and poured by small portions into a mixture of ice and solution of sodium hydroxide (44 g) in water (200 ml). The product was separated by filtration to furnish 0.637 g of yellow solid. Yield 6%. LC-MS (m/z) 239.0 (MH$^+$); $t_R$=2.76.

Method B. To a warm (65° C.) stirred solution of 4-(4,6-Dimethylpyrimidin-2-yl)-morpholine (4 g, 20.7 mmol) in trifluoroacetic acid (100 ml) sodium nitrate (3.52 g, 41.4 mmol) was added. After 3 h more sodium nitrate was added (1.8 g, 20.7 mmol) and the reaction mixture was kept at 65° overnight. It was carefully poured by portions into 10% aqueous sodium carbonate (600 ml) and the product was separated by filtration. Yield 1.637 g, 33%. LC-MS (m/z) 238.9 (MH$^+$); $t_R$=2.70. $^1$H NMR (500 MHz, DMSO-d$_6$): 2.44 (s, 6H), 3.65 (m, 4H), 3.83 (m, 4H).

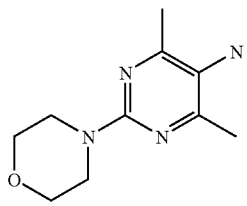

4,6-Dimethyl-2-morpholin-4-yl-pyrimidin-5-ylamine

The suspension of 4-(4,6-dimethyl-5-nitropyrimidin-2-yl)-morpholine (2.2 g, 9.23 mmol), 5% palladium on activated carbon (50% wet, 1.09 g), ammonium formate (8.76 g) was sealed in the Emrys process vial and heated at 150° C. under microwave irradiation for 2 min. The reaction mixture was filtered and evaporated. The residue was treated with ethyl acetate and filtered to give 1.62 g of orange crystalline product after evaporation in vacuo. Yield 84%. LC-MS (m/z) 208.9 (MH$^+$); $t_R$=0.44. $^1$H NMR (500 MHz, DMSO-d$_6$): 2.2 (s, 6H), 3.44 (m, 4H), 3.62 (m, 4H), 4.19 (br, 2H, NH$_2$).

Compounds of the Invention

Acid addition salts of the compounds of the invention may easily be formed by methods known to the person skilled in the art.

Example 1

1a N-[4-Amino-6-methyl-2-(4-trifluoromethylbenzylamino)-pyrimidin-5-yl]-2-cyclopentylacelamide

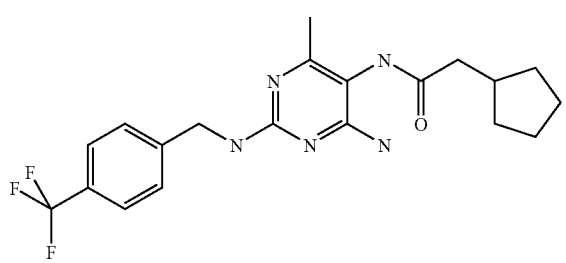

To a cold stirred solution (ice/water bath) of 6-methyl-N*2*-(4-trifluoromethyl-benzyl)-pyrimidine-2,4,5-triamine (119 mg, 0.401 mmol) in acetonitril (3 ml), cyclopentylacetyl chloride (59 mg, 0.402 mmol) was added dropwise in 2 min. Cold bath was removed and stirring continued for 20 min. The obtained suspension was quenched with water (85 ml) and 10% aqueous sodium carbonate (0.5 ml). Organic volatiles were removed under reduced pressure, ethyl acetate (0.5 ml) was added and the mixture was quenched with heptane (20 ml). The obtained biphasic suspension was filtered. The product was washed with water and heptane, dried in vacuo to give 40 mg of pale yellow solid. Yield 25%. LC-MS (m/z) 408.3 (MH$^+$); $t_R$=2.11. $^1$H NMR (500 MHz, DMSO-d$_6$): 1.17 (m, 2H), 1.50 (m, 2H), 1.59 (m, 2H), 1.74 (m, 2H), 1.93 (s, 3H), 2.2 (m, 1H), 2.25 (d, 2H), 4.5 (d, 2H), 5.96 (br, 2H, NH$_2$), 6.96 (br, 1H, NH), 7.5 (d, 2H), 7.64 (d, 2H), 8.57 (s, 1H, NHCO).

1b N-[4-Amino-6-methyl-2-(4-trifluoromethylbenzylamino)-pyrimidin-5-yl]-3,3-dimethylbutyramide

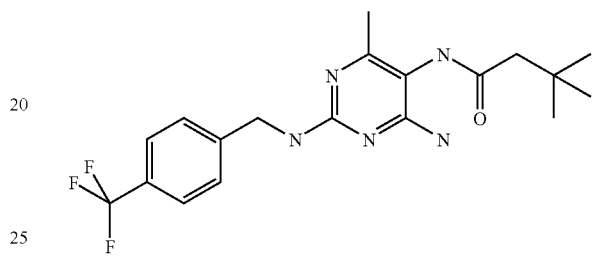

To a cold stirred solution (ice/water bath) of 6-methyl-N*2*-(4-trifluoromethyl-benzyl)-pyrimidine-2,4,5-triamine (341 mg, 1.15 mmol) in acetonitril (7.5 ml), tert-butylacetyl chloride (0.16 ml, 1.15 mmol) was added dropwise in 2 min. Cold bath was removed and stirring continued for 45 min. The obtained reaction mixture was poured into SCX column (10 g, H$^+$ form), washed with acetonitrile (20 ml), methanol (100 ml), and the product was eluted with 4M NH$_3$ in methanol (60 ml). The volatiles were removed in vacuo and the crude product was purified by flash chromatography on silica gel (20 g) with gradient heptane-ethyl acetate to give 153 mg of solid. Yield 33.7%. LC-MS (m/z) 395.9 (MH$^+$); $t_R$=2.00. $^1$H NMR (500 MHz, DMSO-d$_6$): 1.02 (s, 9H), 1.96 (s, 3H), 2.15 (s, 2H), 4.5 (d, 2H), 5.9 (br, 2H, NH$_2$), 6.97 (br, 1H, NH), 7.5 (d, 2H), 7.65 (d, 2H), 8.57 (s, 1H, NHCO).

The following compounds were prepared analogously using corresponding acid chlorides:

1c N-[4-Amino-6-methyl-2-(4-trifluoromethylbenzylamino)-pyrimidin-5-yl]-2-(4-fluorophenyl)-acetamide

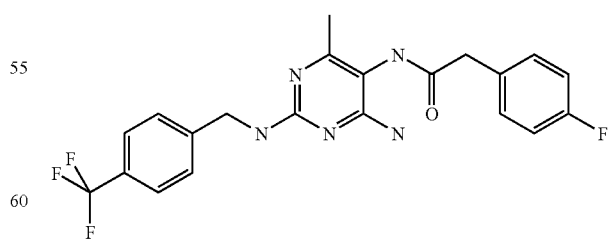

Yield 12%. LC-MS (m/z) 434.3 (MH$^+$); $t_R$=2.07. $^1$H NMR (500 MHz, DMSO-d$_6$): 1.81 (s, 3H), 3.57 (d, 2H), 4.49 (d, 2H), 6.08 (br, 2H, NH$_2$), 6.96 (br, 1H, NH), 7.13 (t, 2H), 7.36 (dd, 2H), 7.49 (d, 2H), 7.64 (d, 2H), 8.83 (s, 1H, NHCO).

1d Hexanoic acid [4-amino-6-methyl-2-(4-trifluoromethylbenzylamino)-pyrimidin-5-yl]-amide

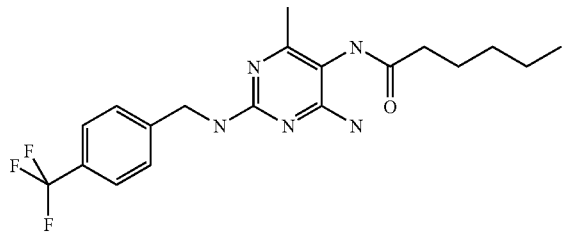

Yield 39.7 mg, 50%. LC-MS (m/z) 396.1 (MH$^+$); $t_R$=2.08. $^1$H NMR (500 MHz, DMSO-d$_6$): 0.87 (t, 3H), 1.28 (m, 4H), 1.56 (qui, 2H), 1.91 (s, 3H), 2.24 (t, 2H), 4.49 (d, 2H), 5.98 (br, 2H, NH$_2$), 6.95 (br, 1H, NH), 7.5 (d, 2H), 7.65 (d, 2H), 8.55 (s, 1H, NHCO).

1e N-[4-Amino-6-methyl-2-(4-trifluoromethylbenzylamino)-pyrimidin-5-yl]-2-(3-chlorophenyl)-acetamide

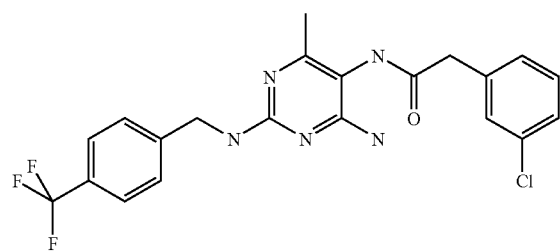

Yield 45.4 mg, 50%. LC-MS (m/z) 450.1 (MH$^+$); $t_R$=2.17. $^1$H NMR (500 MHz, DMSO-d$_6$): 1.82 (s, 3H), 3.61 (s, 2H), 4.49 (d, 2H), 6.12 (br, 2H, NH$_2$), 6.97 (br, 1H, NH), 7.3 (m, 2H), 7.35 (t, 1H), 7.41 (s, 1H), 7.49 (d, 2H), 7.64 (d, 2H), 8.87 (s, 1H, NHCO).

Example 2

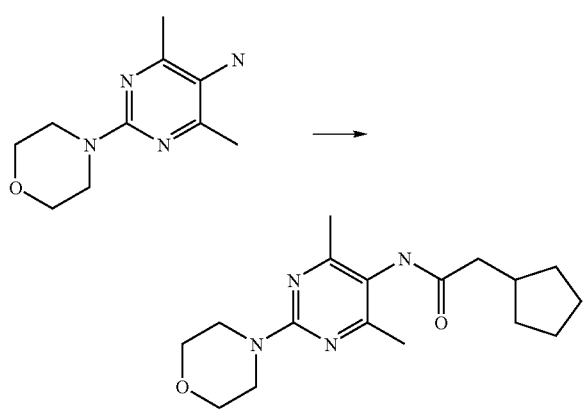

2a 2-Cyclopentyl-N-(4,6-dimethyl-2-morpholin-4-yl-pyrimidin-5-yl)-acetamide To a cold (ice/water bath) stirred solution of 4,6-Dimethyl-2-morpholin-4-yl-pyrimidin-5-ylamine (2.04 g, 9.79 mmol) in acetonitrile (40 ml) cyclopentylacetyl chloride (1.65 ml, 11.75 mmol) was added. The cold bath was removed and the reaction mixture was stirred at r.t. for 30 min. It was poured into sat. aq. sodium hydrogencarbonate (100 ml) and water and filtered. The obtained solid was recrystallized from acetonitrile to give 1.877 g of colorless solid. Yield 60%. LC-MS (m/z) 318.9 (MH$^+$); $t_R$=1.80. $^1$H NMR (500 MHz, DMSO-d$_6$): 1.21 (m, 2H), 1.52 (m, 2H), 1.61 (m, 2H), 1.76 (m, 2H), 2.15 (s, 6H), 2.25 (m, 1H), 2.28 (d, 2H), 3.63 (m, 4H), 3.65 (m, 4H).

2b N-(4,6-Dimethyl-2-morpholin-4-yl-pyrimidin-5-yl)-3,3-dimethylbutyramide

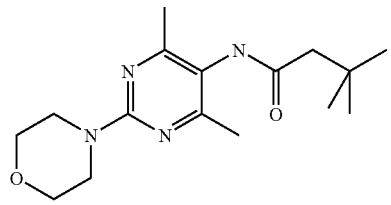

To a solution of 4,6-dimethyl-2-morpholin-4-ylpyrimidin-5-ylamine (2.1 g, 10.4 mmol) in acetonitrile (30 ml) and triethylamine (2.9 ml, 20.8 mmol) tert-butylacetyl chloride (2.9 ml, 20.8 mmol) was added dropwise. After 90 min the reaction mixture was quenched with water and extracted with ethyl acetate twice. The organic phase was washed with sat. aq. sodium hydrogencarbonate (100 ml), dried over magnesiumsulfate and purified by flash chromatography on SiO$_2$ (20 g, gradient heptane-ethyl acetate). The obtained crude product was recrystalized from hot toluene to furnish 946 mg of colorless solid. Yield 30%. LC-MS (m/z) 307.9 (MH$^+$); $t_R$=1.69. $^1$H NMR (500 MHz, DMSO-d$_6$): 1.04 (s, 9H), 2.16 (s, 6H), 2.19 (s, 2H), 3.64 (m, 8H), 9.13 (s, 1H).

The following compound was prepared analogously from corresponding acid chloride:

2c N-(4,6-Dimethyl-2-morpholin-4-ylpyrimidin-5-yl)-2-(4-fluorophenyl-acetamide

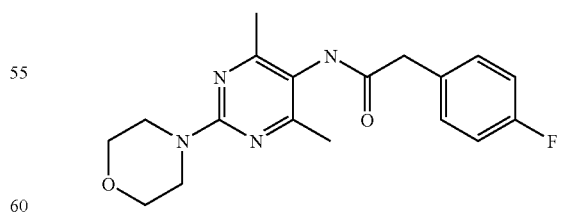

The title compound was recrystallised from hot ethyl acetate after flash chromatography purification. Yield 1.193 g, 37%. LC-MS (m/z) 345.1 (MH$^+$); $t_R$=1.81. $^1$H NMR (500 MHz, DMSO-d$_6$): 2.09 (s, 6H), 3.6-3.66 (overlapping m, 10H), 7.16 (t, 2H), 7.38 (dd, 2H), 9.42 (s, 1H).

2d 2-(3,4-Difluorophenyl)-N-(4,6-dimethyl-2-morpholin-4-ylpyrimidin-5-yl)-acetamide

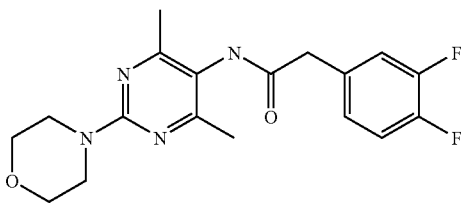

To a cold (ice/water bath) stirred solution of 4,6-dimethyl-2-morpholin-4-yl-pyrimidin-5-ylamine (52.4 mg, 0.25 mmol) in acetonitrile (1 ml) 3,4-difluorophenylacetyl chloride (0.065 ml, 0.3 mmol) was added. The reaction mixture was kept at 60° C. for 1 min and allowed to cool. It was poured into SCX-column (10 g, $H^+$-form), washed with acetonitrile and methanol and eluted with 4 M $NH_3$ in methanol. After evaporation the crude product was precipitated from concentrated solution in ethyl acetate with heptane and filtered to give 34 mg of colorless solid. Yield 37%. LC-MS (m/z) 363.3 ($MH^+$); $t_R$=1.96. $^1H$ NMR (500 MHz, DMSO-$d_6$): 2.09 (s, 6H), 3.63 (m, 10H), 7.19 (m, 1H), 7.38 (m, 1H), 7.41 (m, 1H), 9.43 (s, 1H).

The following compounds were prepared analogously using appropriate acid chlorides:

2e N-(4,6-Dimethyl-2-morpholin-4-ylpyrimidin-5-yl)-2-(3-fluorophenyl)-acetamide

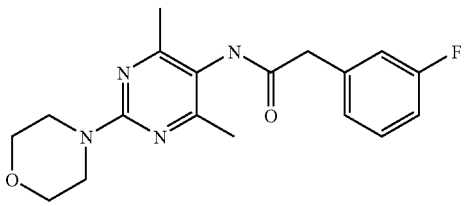

The title compound was purified by flash chromatography on $SiO_2$ (20 g, gradient heptane-ethyl acetate). Yield 27 mg, 31%. LC-MS (m/z) 345.0 ($MH^+$); $t_R$=1.83. $^1H$ NMR (500 MHz, DMSO-$d_6$): 2.09 (s, 6H), 3.62 (m, 4H), 3.64 (m, 4H), 3.66 (s, 2H), 7.08 (dt, 1H), 7.18 (overlapping dd, 1H), 7.19 (overlapping d, 1H), 7.38 (dt, 1H), 9.45 (s, 1H).

2f Hexanoic acid (4,6-dimethyl-2-morpholin-4-ylpyrimidin-5-yl)-amide

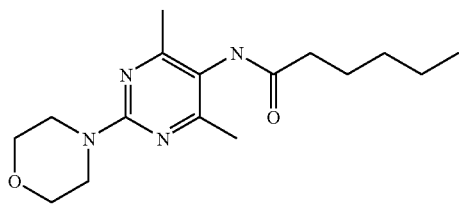

The title compound was purified by flash chromatography on $SiO_2$ (20 g, gradient heptane-ethyl acetate). Yield 49 mg, 64%. LC-MS (m/z) 307.2 ($MH^+$); $t_R$=1.84. $^1H$ NMR (500 MHz, DMSO-$d_6$): 0.88 (t, 3H), 1.31 (m, 4H), 1.60 (qui, 2H), 2.14 (s, 6H), 2.28 (t, 2H), 3.63 (m, 4H), 3.65 (m, 4H), 9.16 (s, 1H).

TABLE 1

Reagents used for the preparation of compounds.

| Name | Supplier | CAS no. | Cat. no. |
|---|---|---|---|
| 2-Chloro-6-methyl-5-nitro-pyrimidin-4-ylamine | Pfaltz-Bauer | 5453-06-5 | A19620 |
| 4-Trifluoromethyl-benzylamine | Aldrich | 3300-51-4 | 26,350-8 |
| Zinc (powder, <10 micron) | Aldrich | 52374-36-4 | 20,998-8 |
| Cyclopentylacetyl chloride | Lancaster | 1122-99-2 | 14562 |
| tert-Butylacetyl chloride | Aldrich | 7065-46-5 | B8,880-2 |
| Morpholinoformamidine hydrobromide | ABCR | 157415-17-3 | AV19985 |
| Potassium tert-butoxide | Aldrich | 865-47-4 | 15,667-1 |
| Acetylacetone | Aldrich | 123-54-6 | P775-4 |
| 4-Fluorophenylacetyl chloride | Aldrich | 459-04-1 | 46,695-6 |
| 3-Chlorophenylacetic acid | Aldrich | 1878-65-5 | C6,335-9 |
| Ammonium formate | Aldrich | 540-69-2 | 15,626-4 |
| Palladium, 5% on activated carbon, wet | Aldrich | 7440-05-3 | 27,670-7 |
| 3,4-Difluorophenylacetic acid | ABCR | 658-93-5 | F02874E |
| 3-Fluorophenylacetic acid | Aldrich | 331-25-9 | 24,804-5 |

In Vitro and In Vivo Testing

The compounds of the invention have been tested and shown effect in one or more of the below models:

Relative Efflux Through the KCNQ2 Channel

This exemplifies a KCNQ2 screening protocol for evaluating compounds of the present invention. The assay measures the relative efflux through the KCNQ2 channel, and was carried out according to a method described by Tang et al. (Tang, W. et. al., *J. Biomol. Screen.* 2001, 6, 325-331) for hERG potassium channels with the modifications described below.

An adequate number of CHO cells stably expressing voltage-gated KCNQ2 channels were plated at a density sufficient to yield a mono-confluent layer on the day of the experiment. Cells were seeded on the day before the experiment and loaded with 1 μCi/ml [$^{86}Rb$] over night. On the day of the experiment cells were washed with a HBSS-containing buffer. Cells were pre-incubated with drug for 30 minutes and the $^{86}Rb^+$ efflux was stimulated by a submaximal concentration of 15 mM KCl in the continued presence of drug for additional 30 minutes. After a suitable incubation period, the supernatant was removed and counted in a liquid scintillation counter (Tricarb). Cells were lysed with 2 mM NaOH and the amount of $^{86}Rb^+$ was counted. The relative efflux was calculated $((CPM_{super}/(CPM_{super}+CPM_{cell}))_{Cmpd}/(CPM_{super}/(CPM_{super}+CPM_{cell}))_{15mM\ KCl})*100-100$.

The compounds of the invention have an $EC_{50}$ of less than 20000 nM, in most cases less than 2000 nM and in many cases less than 200 nM. Accordingly, the compounds of the invention are considered to be useful in the treatment of diseases associated with the KCNQ family potassium channels.

Electrophysiological Patch-Clamp Recordings

Voltage-activated KCNQ2 currents were recorded from mammalian CHO cells by use of conventional patch-clamp recordings techniques in the whole-cell patch-clamp configuration (Hamill O P et. al. *Pflügers Arch* 1981; 391: 85-100). CHO cells with stable expression of voltage-activated KCNQ2 channels were grown under normal cell culture conditions in $CO_2$ incubators and used for electrophysiological recordings 1-7 days after plating. KCNQ2 potassium channels were activated by voltage steps up to +80 mV in increments of 5-20 mV (or with a ramp protocol) from a membrane holding potential between −100 mV and −40 mV (Tatulian L et al. *J Neuroscience* 2001; 21 (15): 5535-5545). The electrophysiological effects induced by the compounds were evaluated on various parameters of the voltage-activated KCNQ2 current. Especially effects on the activation threshold for the current and on the maximum induced current were studied.

Some of the compounds of the invention have been tested in this test. A left-ward shift of the activation threshold or an increase in the maximum induced potassium current is expected to decrease the activity in neuronal networks and thus make the compounds useful in diseases with increased neuronal activity—like epilepsia.

Maximum Electroshock

The test was conducted in groups of male mice using corneal electrodes and administering a square wave current of 26 mA for 0.4 seconds in order to induce a convulsion characterised by a tonic hind limb extension (Wlaz et al. *Epilepsy Research* 1998, 30, 219-229).

Pilocarpine Induced Seizures

Pilocarpine induced seizures are induced by intraperitoneal injection of pilocarpine 250 mg/kg to groups of male mice and observing for seizure activity resulting in loss of posture within a period of 30 minutes (Starr et al. *Pharmacology Biochemistry and Behavior* 1993, 45, 321-325).

Electrical Seizure—Threshold Test

A modification of the up-and-down method (Kimball et al. *Radiation Research* 1957, 1-12) was used to determine the median threshold to induce tonic hind-limb extension in response to corneal electroshock in groups of male mice. The first mouse of each group received an electroshock at 14 mA, (0.4 s, 50 Hz) and was observed for seizure activity. If a seizure was observed the current was reduced by 1 mA for the next mouse, however, if no seizure was observed then the current was increased by 1 mA. This procedure was repeated for all 15 mice in the treatment group.

Chemical Seizure—Threshold Test

The threshold dose of pentylenetetrazole required to induce a clonic convulsion was measured by timed infusion of pentylenetetrazole (5 mg/mL at 0.5 mL/minute) into a lateral tail vein of groups of male mice (Nutt et al. *J Pharmacy and Pharmacology* 1986, 38, 697-698).

Amygdala Kindling

Rats underwent surgery to implantation of tri-polar electrodes into the dorsolateral amygdala. After surgery the animals were allowed to recover before the groups of rats received either varying doses of test compound or the drug's vehicle. The animals were stimulated with their initial after discharge threshold+25 µA daily for 3-5 weeks and on each occasion seizure severity, seizure duration, and duration of electrical after discharge were noted. (Racine. *Electroencephalography and Clinical Neurophysiology* 1972, 32, 281-294).

Side Effects

Central nervous system side-effects were measured by measuring the time mice would remain on rotarod apparatus (Capacio et al. *Drug and Chemical Toxicology* 1992, 15, 177-201); or by measuring their locomotor activity by counting the number of infra-red beams crossed in a test cage (Watson et al. *Neuropharmacology* 1997, 36, 1369-1375). Hypothermic actions on the animals core body temperature of the compound were measured by either rectal probe or implanted radiotelemetry transmitters capable of measuring temperature (Keeney et al. *Physiology and Behaviour* 2001, 74, 177-184).

Pharmacokinetics

The pharmacokinetic properties of the compounds were determined via. i.v. and p.o. dosing to Spraque Dawley rats, and, thereafter, drawing blood samples over 20 hours. Plasma concentrations were determined with LC/MS/MS.

The invention claimed is:

1. A compound selected from the group consisting of:
N-[4-Amino-6-methyl-2-(4-trifluoromethylbenzylamino)-pyrimidin-5-yl]-2-cyclopentylacetamide,
N-[4-Amino-6-methyl-2-(4-trifluoromethylbenzylamino)-pyrimidin-5-yl]-3,3-dimethylbutyramide,
N-[4-Amino-6-methyl-2-(4-trifluoromethylbenzylamino)-pyrimidin-5-yl]-2-(4-fluorophenyl)-acetamide,
Hexanoic acid [4-amino-6-methyl-2-(4-trifluoromethylbenzylamino)-pyrimidin-5-yl]-amide,
N-[4-Amino-6-methyl-2-(4-trifluoromethylbenzylamino)-pyrimidin-5-yl]-2-(3-chlorophenyl)-acetamide,
2-Cyclopentyl-N-(4,6-dimethyl-2-morpholin-4-yl-pyrimidin-5-yl)-acetamide,
N-(4,6-Dimethyl-2-morpholin-4-yl-pyrimidin-5-yl)-3,3-dimethylbutyramide,
N-(4,6-Dimethyl-2-morpholin-4-ylpyrimidin-5-yl)-2-(4-fluorophenyl)-acetamide,
2-(3,4-Difluorophenyl)-N-(4,6-dimethyl-2-morpholin-4-ylpyrimidin-5-yl)-acetamide,
N-(4,6-Dimethyl-2-morpholin-4-ylpyrimidin-5-yl)-2-(3-fluorophenyl)-acetamide and
Hexanoic acid (4,6-dimethyl-2-morpholin-4-ylpyrimidin-5-yl)-amide;
or a pharmaceutically acceptable salt thereof.

2. A pharmaceutical composition comprising a compound according to claim 1 in a therapeutically effective amount together with one or more pharmaceutically acceptable carriers or diluents.

3. A compound having the general formula I:

(I)

wherein: q is 0 or 1;
$R^1$ and $R^2$ taken together with the nitrogen to which they are attached form a 5 to 7 membered ring optionally containing a further heteroatom that is oxygen;
$R^3$ and $R^4$ are independently selected from hydrogen, halogen, cyano, amino, $C_{1-6}$-alk(en/yn)yl, $C_{3-8}$-cycloalk(en)yl, halo-$C_{1-6}$-alk(en/yn)yl, halo-$C_{3-8}$-cycloalk(en)yl, $C_{1-6}$-alk(en/yn)yloxy, $C_{3-5}$-cycloalk(en)yloxy, $C_{3-5}$-cycloalk(en)yl-$C_{1-6}$-alk(en/yn)yl oxy, halo-$C_{1-6}$-alk(en/yn)yloxy, halo-$C_{3-8}$-cycloalk(en)yloxy and halo-$C_{3-5}$-cycloalk(en)yl-$C_{1-6}$-alk(en/yn)yloxy, provided that $R^3$ and $R^1$ are not both hydrogen;
$R^5$ is selected from the group consisting of $C_{1-10}$-alk(en/yn)yl, $C_{3-8}$-cycloalk(en)yl-$C_{1-6}$-alk(en/yn)yl, optionally substituted aryl-$C_{1-6}$-alk(en/yn)yl and optionally substituted aryl;
or a pharmaceutically acceptable salt thereof.

4. The compound according to claim 3, wherein the ring is a 6 membered ring.

5. The compound according to claim 4, wherein the ring is a morpholine ring.

* * * * *

UNITED STATES PATENT AND TRADEMARK OFFICE
CERTIFICATE OF CORRECTION

PATENT NO. : 7,683,058 B2  Page 1 of 1
APPLICATION NO. : 11/516221
DATED : March 23, 2010
INVENTOR(S) : Nikolay Khanzhin et al.

It is certified that error appears in the above-identified patent and that said Letters Patent is hereby corrected as shown below:

In Col. 30, claim 3, line 50, replace "C3-5-cycloalk(en)yloxy, C3-5-cy-" with --C3-8-cycloalk(en)yloxy, C3-8-cy- --.

In Col. 30, claim 3, line 52, replace "and halo-$C_{3-5}$-" with --and halo-C3-5- --.

Signed and Sealed this

Twenty-ninth Day of June, 2010

David J. Kappos
*Director of the United States Patent and Trademark Office*